United States Patent [19]
Aquila et al.

[11] 3,966,827
[45] June 29, 1976

[54] PRODUCTION OF 3-METHYLPENTANE-1,5-DIOL

[75] Inventors: Werner Aquila, Mannheim; Walter Himmele, Walldorf; Werner Fliege, Otterstadt; Hardo Siegel, Ludwigshafen, all of Germany

[73] Assignee: BASF Aktiengesellschaft, Ludwigshafen (Rhine), Germany

[22] Filed: Jan. 16, 1975

[21] Appl. No.: 541,638

[30] Foreign Application Priority Data

Jan. 30, 1974  Germany............................ 2404312

[52] U.S. Cl. .......................... 260/635 E; 260/75 R; 260/77.5 R; 260/78 R; 260/345.9; 260/583 P
[51] Int. Cl.² ........................................ C07C 29/00
[58] Field of Search ......... 260/345.9, 635 E, 635 A, 260/635 R, 632 HF

[56] References Cited
UNITED STATES PATENTS

| | | | |
|---|---|---|---|
| 2,694,077 | 11/1954 | Standsbury et al. ............ | 260/635 A |
| 3,168,579 | 2/1965 | Poswell et al. .................. | 260/635 A |
| 3,438,997 | 4/1969 | Fetterly et al. .................. | 260/345.9 |
| 3,530,190 | 9/1970 | Olivier ............................ | 260/635 R |
| 3,555,098 | 1/1971 | Olivier et al. ................... | 260/632 HF |

OTHER PUBLICATIONS

T904021, Copelin, 11–21–72, 260/635 A.

*Primary Examiner*—Joseph E. Evans
*Attorney, Agent, or Firm*—Johnston, Keil, Thompson & Shurtleff

[57] ABSTRACT

The production of 3-methylpentane-1,5-diol by hydroformylation of 2-methylbut-1-en-4-ol with carbon monoxide and hydrogen at elevated temperature and superatmospheric pressure in the presence of a rhodium carbonyl complex which has been modified by a tertiary organic phosphine followed by hydrogenation of the 2-hydroxy-4-methyltetrahydropyran at elevated temperature and superatmospheric pressure in the presence of a hydrogenation catalyst.

13 Claims, No Drawings

PRODUCTION OF 3-METHYLPENTANE-1,5-DIOL

This application discloses and claims subject matter described in German Patent Application P 24 04 312.7, filed Jan. 30, 1974 which is incorporated herein by reference.

The present invention relates to a new process for the production of 3-methylpentane-1,5-diol.

It is known that this compound can be prepared by Diels-Alder addition of vinyl methyl ether to crotonaldehyde followed by hydrogenation of the 3,4-dihydro-2-methoxy-4-methyl-2H-pyran first obtained (Organic Syntheses, volume 34 (1954), pages 29f and 71f). This process is not however suitable for commercial operation because the starting compounds have only limited accessibility.

The invention therefore has for its object to prepare in a more economical manner 3-methylpentane-1,5-diol which is an important starting material, particularly for the production of polyurethanes.

We have found that 3-methylpentane-1,5-diol is obtained advantageously by reacting 2-methylbut-1-en-4-ol with carbon monoxide at elevated temperature and at superatmospheric pressure in the presence of a rhodium carbonyl complex which has been modified by a tertiary organic phosphine and hydrogenating the resultant 2-hydroxy-4-methyltetrahydropyran at elevated temperature and superatmospheric pressure in the presence of a hydrogenation catalyst to form 3-methylpentane-1,5-diol.

The new process has the advantage that 3-methylpentane-1,5-diol is made accessible industrially in good yields in a simple manner.

The starting compound 2-methylbut-1-en-4-ol is easily accessible by condensation of isobutene with formaldehyde (cf. German Patent 1,275,049).

Carbon monoxide and hydrogen are preferably used for the hydroformylation in a ratio by volume of from 1:0.25 to 1:4 and particularly in the ratio by volume of from 1:0.5 to 1:2. The said gas mixture is used as a rule at least in a stoichiometric amount based on 2-methylbut-1-en-4-ol but advantageously in an excess of up to 200% molar.

The hydroformylation is advantageously carried out at a temperature of from 60° to 140°C. Temperatures of from 70° to 110°C have proved to be particularly suitable. The reaction proceeds at a pressure of only a few atmospheres, for example at 10 atmospheres. In order to obtain satisfactory space-time yields in this case it is necessary however to use high concentrations of rhodium in the reaction mixture. It is therefore advantageous to use a pressure of from 80 to 700 atmospheres in the hydroformylation.

The rhodium complexes modified with tertiary organic phosphines are advantageously used in an amount of from 0.5 to 500 ppm and particularly from 1 to 50 ppm calculated as rhodium metal and based on 2-methylbut-1-en-4-ol. The tertiary organic phosphines used as modifying agents preferably have as substituents alkyl radicals of one to twenty carbon atoms, cycloalkyl radicals of five to eight carbon atoms and also phenyl groups which may contain one or two alkyl groups of one to 4 carbon atoms or alkoxy groups of one to four carbon atoms as substituents. Examples of particularly suitable phosphines are triphenyl phosphine, trianisyl phosphine, tri-p-tolyl phosphine, tri-n-butyl phosphine and tricyclohexyl phosphine. Triphenyl phosphine is especially suitable because of its easy accessibility.

Particularly good yields of 2-hydroxy-4-methyltetrahydropyran are obtained when at least 3 moles of the said phosphines are used per gram atom of rhodium. An atomic ratio of rhodium to phosphorus of from 1:5 to 1:30 has proved to be particularly advantageous. Although the exact composition of the catalytically active rhodium catalyst complex is not known it is assumed that it is a rhodium carbonyl or a rhodium carbonyl hydride in which one or more carbonyl ligands is/are replaced by tertiary organic phosphine(s).

Rhodium carbonyl or a rhodium carbonyl olefin complex may be treated respectively with an appropriate amount of tertiary phosphine or carbon monoxide. The catalytically active rhodium complex is however advantageously produced from a suitable rhodium compound such as dimeric cyclooctadienyl rhodium chloride, rhodium oxide, rhodium chloride or a rhodium salt of a fatty acid in situ in the reaction mixture with the appropriate amounts of tertiary phosphine and carbon monoxide.

Additional solvent is not used as a rule. The 2-methylbut-1-en-4-ol then serves as solvent. It is also possible however to use a solvent which is inert under the reaction conditions such as an alkanol, for example butanol, an ether such as tetrahydrofuran or a hydrocarbon such as cyclohexane.

The reaction period may be chosen so that there is a substantially complete conversion of the 2-methylbut-1-en-4-ol into 2-hydroxy-4-methyltetrahydropyran. The reaction period is then from six to forty-eight hours depending on the concentration of catalyst. On the other hand it is possible to hydroformylate only a portion of the 2-methylbut-1-en-4-ol, to separate 2-hydroxy-4-methyl-tetrahydropyran from the reaction mixture and to return the unreacted 2-methyl-but-1-en-4-ol to the reaction.

A special purification of the 2-hydroxy-4-methyltetrahydropyran obtained as reaction product is not necessary. It is however advisable to separate the phosphine used by distillation prior to hydrogenation. When operating with partial conversion it is convenient to remove the unreacted 2-methylbut-1-en-4-ol by fractionation as the low-boiling fraction after which the 2-hydroxy-4-methyltetrahydropyran is separated from the residue by distillation. The residue in which the catalyst is contained may be used again for hydroformylation. If very pure 3-methylpentane-1,5-diol is required, it is advisable to purify the 2-hydroxy-4-methyltetrahydropyran by a fractional distillation prior to the further hydrogenation because the purification of the 3-methylpentane-1,5-diol is thus made simpler.

The 2-hydroxy-4-methyltetrahydropyran obtained by hydroformylation is hydrogenated to 3-methylpentane-1,5-diol. The hydrogenation is conveniently carried out without any diluent. Conventional hydrogenation catalyst are used for the hydrogenation. Catalysts containing cobalt and nickel and which may also contain activating additives such as copper, chromium and manganese, have proved to be particularly suitable. Suitable hydrogenation catalysts also include those known as Atkin catalysts based on cuprochromium oxide. The catalysts based on cuprochromium oxide. The catalysts may be used as unsupported catalysts, for example as Raney nickel or Raney cobalt, but it is also possible for the catalyst metal to be deposited on a carrier. Examples of suitable carriers are silicic acid, silica gel, aluminum oxide and pumice. These supported catalysts may for example contain the catalytically active metal in an amount of from 2 to 40% by weight.

Although hydrogenation may be carried out without using a solvent it is possible to use water or a cyclic ether such as tetrahydrofuran or dioxane as a solvent. Hydrogenation is advantageously carried out at a temperature of from 60° to 250°C. Temperatures of from 80° to 180°C are preferred. Pressures of from 20 to 300 atmospheres are as a rule maintained in the hydrogenation. Pressures of from 50 to 200 atmospheres have proved to be particularly suitable. It is advisable to maintain a hydrogen partial pressure of from 50 to 150 atmospheres in the hydrogenation in order to obtain good yields.

The 3-methylpentane-1,5-diol is obtained in pure form as a water-white viscous liquid which is miscible in all proportions with water by fractional distillation with or without previous separation of the catalyst and distilling off the solvent used. It dissolves in lower alcohols and cyclic ethers but is insoluble in hydrocarbons such as hexane, heptane and cyclohexane.

3-methylpentane-1,5-diol prepared according to the process of the invention is suitable for the production of polyesters and polyurethanes. It is particularly suitable for the production of polyurethanes because it decreases the tendency for crystallization and has a certain plasticizing effect as a polyurethane component. 3-methylpentane-1,5-diol is also suitable as an intermediate for the production of 3-methyl-1,5-pentamethylenediamine which is suitable as a starting material for the manufacture of polyamides.

The process according to the invention is illustrated in the following Examples.

a. The production of 2-hydroxy-4-methyltetrahydropyran:

EXAMPLE 1

1500 g of 2-methyl-1-buten-4-ol and 0.1 g of rhodium cyclooctadienyl chloride complex are introduced together with 2 g of triphenyl phosphine into a rotating autoclave having a capacity of 3000 ml. The gas space of the autoclave, after it has been closed, is flushed with nitrogen and then charged cold with an equimolar mixture of carbon monoxide and hydrogen up to a pressure of 50 atmospheres. The reaction mixture is then heated to 80°C after which the pressure of carbon monoxide and hydrogen is adjusted to 250 atmospheres. The portion of gas used up is replaced by supplying more each hour. 915 atmospheres of gas is forced in within a period of thirty-eight hours. 1950 g of reaction mixture is obtained after cooling and releasing the pressure.

After the catalyst has been separated in a falling film evaporator the product is worked up by fractional distillation. 11 g of evaporator residue is obtained which contains the whole of the rhodium and phosphine used. This residue may be used again as a catalyst for the hydroformylation of 2-methyl-2-buten-4-ol. 1884 g of distillate from the falling film distillation is fractionated in a ten-tray column at a pressure of 30 mm. In a temperature range (at the top) of from 55° to 94°C the amount passing over is 198 g and according to gas-chromatographic analysis this consists predominantly of 2-methyl-1-buten-4-ol. 173 parts pass over at from 94° to 100°C. This consists to the extent of 85% of 2-hydroxy-4-methyltetrahydropyran and 10% of 2-methyl-1-buten-4-ol.

1390 g of 2-hydroxy-4-methyltetrahydropyran having a purity of more than 99% is obtained at 100°C/30 mm.

Disregarding the product remaining in the distillation residue, 1537 g of 2-hydroxy-4-methyl-tetrahydropyran is obtained. This is equivalent to a yield of 88.3% based on reacted 2-methyl-1-buten-4-ol.

EXAMPLE 2

The procedure described in Example 1 is repeated but 2 g of trianisyl phosphine is used. The absorption of gas in fifty-three hours is 910 atmospheres. The discharge of 1900 g from the reaction is fractionated immediately in a ten-tray column.

305 g of 2-methyl-1-buten-4-ol is obtained which passes over at from 58° to 62°C at 30 mm. 1474 of 2-hydroxy-4-methyltetrahydropyran passes over at from 99° to 100°C at 30 mm (distillation residue: 60 g). The yield of 2-hydroxy-4-methyltetrahydropyran is 91.2% based on reacted 2-methyl-1-buten-4-ol.

EXAMPLE 3

In the manner described in Example 1 1500 g of methylbutenol is reacted with the same amount (0.1 g) of rhodium cyclooctadienyl chloride and 2 g of tris-p-tolyl phosphine at 80°C with an equimolar mixture of carbon monoxide and hydrogen at a pressure of 250 atmospheres. The gas absorption over eighty-three hours is 930 atmospheres. The hydroformylation product (1870 g) obtained is worked up in the same manner. 346 g of methylbutenol is recovered. 1416 g of 2-hydroxy-4-methyl-tetrahydropyran is obtained. Taking into account the unreacted portion of 2-methyl-1-buten-4-ol the yield is 91%.

EXAMPLE 4

In the manner described in Example 1, 1500 g of 2-methyl-1-buten-4-ol is reacted in the course of forty-eight hours at 80°C under a pressure of 250 atmospheres ($CO/H_2 = 1:1$) in the presence of 100 mg of rhodium cyclooctadienyl chloride and 0.5 g of triphenyl phosphine as catalyst. A total of 1005 atmospheres is forced in subsequently. The reaction mixture - 1874 g - is fractionated. 180 g of unreacted 2-methyl-1-buten-4-ol is recovered. At from 87° to 88°C at 18 mm there passes over 1552 g of 2-hydroxy-4-methyltetrahydropyran having a purity of more than 99%. The distillation residue is 43 g. The yield of 2-hydroxy-4-methyltetrahydropyran is 87.4% at a conversion of the unsaturated alcohol of 88%.

EXAMPLE 5

1000 g of 2-methyl-1-buten-4-ol, 100 mg of rhodium bis-triphenyl phosphine carbonyl chloride $Rh(Pl_3)_2COCl$ (L = phenyl) and 3 g of triphenylphosphine are caused to react at a pressure of 250 atmospheres and at 80°C with a mixture (1:1) of carbon monoxide and hydrogen. 45 atmospheres of gas is forced in over 12 hours. After raising the temperature to 90°C and increasing the pressure to 270 atmospheres another 95 atmospheres of gas can be forced in over another twelve hours. After a further rise in temperature to 100°C another 190 atmospheres of gas can be forced in and is used up at a pressure of 290 atmospheres. The reaction mixture (1237 g) contains 148 g of unreacted 2-methyl-1-buten-4-ol and gives in fractional distillation 863 g of 2-hydroxy-4-methyltetrahydropyran. The yield of 2-hydroxy-4-methyltetrahydropyran in this experiment is 75 %.

b. Hydrogenation of 2-hydroxy-4-methyltetrahydropyran to 3-methyl-pentane-1,5-diol:

EXAMPLE 6

1000 g of 2-hydroxy-4-methyltetrahydropyran in which 50 g of Raney cobalt has been suspended is introduced into a rotating autoclave having a volume of 3000 ml. The autoclave is flushed with nitrogen and then 50 atmospheres of hydrogen is forced in. The autoclave is heated to 80°C and the pressure of hydrogen is adjusted to 140 atmospheres. A gas absorption of 100 atmospheres can be established by forcing it in hourly over 5 hours. By subsequently raising the pressure and temperature to 90°C/160 atmospheres; 100°C/180 atmospheres and 110°C/200 atmospheres no further absorption of hydrogen is achieved.

After cooling and releasing the pressure, the reaction mixture, which has become very viscous during the hydrogenation, first has its filterability increased by adding 500 g of methanol. The catalyst is separated by filtration and then the methanol is distilled off in a five-tray column at atmospheric pressure. In a fractionation 3-methylpentane-1,5-diol passes over at a pressure of 0.3 mm at from 104° to 105°C. The product obtained in this purification process has a purity of more than 99.8% according to gas chromatographic analysis.

871 g of 3-methylpentane-1,5-diol is obtained; this is equivalent to a yield of diol of 86% based on the 2-hydroxy-4-methyltetrahydropyran used. Further portions of 3-methylpentane-1,5-diol are found (about 35 g) in the distillation residue of 50 g.

EXAMPLE 7

50 g of Raney cobalt is added to 1270 g of 2-hydroxy-4-methyltetrahydropyran and in the course of 10 hours at 80°C at a hydrogen pressure of 150 atmospheres hydrogenation is carried out. The reaction mixture (1327 g) is fractionated in a five-tray column at a pressure of 0.3 mm, the Raney-cobalt having been removed previously by filtration. In a fractionation 67 g of first runnings is obtained. This consists to the extent of 90% of 3-methylpentane-1,5-diol. The main fraction passes over at from 99° to 100°C at 0.3 mm. 1049 g of 99.7% 3-methylpentane-1,5-diol is obtained; this is equivalent to a yield of 81.5%. The distillation residue (32 g) consists predominantly of 3-methylpentane-1,5-diol according to gas-chromatographic analysis.

EXAMPLE 8

735 g of 2-hydroxy-4-methyltetrahydropyran (about 96%, containing 4% of constituents of higher boiling point) is mixed with 114 g of water. The hydrogenation takes place at 80°C at a hydrogen pressure of 150 atmospheres. The reaction mixture (860 g) is freed from catalyst by filtration. 674 g of 97% 3-methylpentane-1,5-diol is obtained by fractional distillation at from 92° to 94°C and 0.2 mm. This is equivalent to a yield of 88% based on the 2-hydroxy-4-methyltetrahydropyran used.

EXAMPLE 9

100 g of 2-hydroxy-4-methyltetrahydropyran is hydrogenated in an autoclave having a capacity of 220 ml with 5 g of copper-chromium oxide catalyst at 80°C/140 atmospheres; 90°C/160 atmospheres; 100°C/180 atmospheres and 110°C/200 atmospheres. The absorption of hydrogen in the second stage is 35 atmospheres in 4 hours, in the third stage 25 atmospheres in 5 hours and in the fourth stage 20 atmospheres in 4 hours. 87 g of reaction mixture is obtained after the pressure of hydrogen has been released.

After filtration carried out by means of activated carbon 51 g of 3-methylpentane-1,5-diol is obtained by fractional distillation. This is equivalent to a yield of 50% based on the cyclic hemiacetal used.

We claim:

1. A process for the production of 3-methylpentane-1,5-diol wherein 2-methylbut-1-en-4-ol is reacted with carbon monoxide and hydrogen at 60–140°C and at 10–700 atmospheres pressure at a ratio by volume of CO to $H_2$ in the range of 1:0.25 to 1:4 in the presence of a rhodium carbonyl complex which has been modified with at least three mols of a tertiary organic phosphine per gram atom of rhodium, the organic groups of said tertiary phosphine being selected from the group consisting of alkyl having 1–20 carbon atoms, cycloalkyl having 5–8 carbon atoms, phenyl, phenyl bearing 1–2 alkyl groups, each having 1–4 carbon atoms, and phenyl bearing 1–2 alkoxy groups, each having 1–4 carbon atoms, said rhodium complex catalyst being present in an amount of 0.5 to 500 ppm, calculated as rhodium metal and based on the 2-methylbut-1-en-4-ol, to produce 2-hydroxy-4-methyltetrahydropyran and the 2-hydroxy-4-methyltetrahydropyran thus obtained is hydrogenated at elevated temperature and at superatmospheric pressure in the presence of a conventional hydrogenation catalyst to form 3-methylpentane-1,5-diol.

2. A process as claimed in claim 1 wherein the said CO to $H_2$ ratio is from 1:0.5 to 1:2.

3. A process as claimed in claim 1 wherein the mixture of carbon monoxide and hydrogen is used in a stoichiometric amount based on 2-methylbut-1-en-4-ol or in an excess of up to 200 mole%.

4. A process as claimed in claim 1 wherein the said temperature is from 70° to 110°C.

5. A process as claimed in claim 1 wherein the pressure during hydroformylation is from 80 to 700 atmospheres.

6. A process as claimed in claim 1 wherein the amount of rhodium complex catalyst is 1 to 50 ppm calculated as rhodium metal and based on 2-methylbut-1-en-4-ol.

7. A process as claimed in claim 1 wherein said tertiary phosphine is triphenyl phosphine.

8. A process as claimed in claim 1 wherein said tertiary phosphine is trianisyl phosphine, tri-p-tolyl phosphine, tri-n-butyl phosphine or tricyclohexyl phosphine.

9. A process as claimed in claim 1 wherein the atomic ratio of rhodium to phosphorus in the catalyst is from 1:5 to 1:30.

10. A process as claimed in claim 1 wherein only a portion of the 2-methylbut-1-en-4-ol is hydroformylated and the unreacted 2-methylbut-1-en-4-ol is returned to the reaction after separation of the 2-hydroxy-4-methyltetrahydropyran.

11. A process as claimed in claim 1 wherein hydrogenation is carried out at from 60° to 250°C and a pressure of 20 to 300 atmospheres.

12. A process as claimed in claim 1 wherein the hydrogenation is carried out at a temperature of from 80° to 180°C and a pressure of from 50 to 200 atmospheres.

13. A process as claimed in claim 1 wherein a hydrogen partial pressure of from 50 to 150 atmospheres is maintained during the hydrogenation.

* * * * *